United States Patent [19]

Adams

[11] Patent Number: 4,543,206

[45] Date of Patent: Sep. 24, 1985

[54] NAIL LACQUER AND ENAMEL REMOVER

[76] Inventor: Cornell L. Adams, 1199 Broad St., Newark, N.J. 07114

[21] Appl. No.: 606,879

[22] Filed: May 3, 1984

[51] Int. Cl.$^4$ .............. A61K 7/047; C11D 7/30; C11D 7/50

[52] U.S. Cl. ................................. 252/557; 134/38; 252/170; 252/171; 252/172; 252/174.21; 252/364; 252/DIG. 8; 424/61

[58] Field of Search ............... 252/153, 162, 163, 164, 252/165, 166, 171, 364, DIG. 8, 557; 424/61; 134/38

[56] References Cited

U.S. PATENT DOCUMENTS

| | | | |
|---|---|---|---|
| 3,094,491 | 6/1963 | Greminger | 252/171 |
| 3,856,695 | 12/1974 | Geiss | 252/162 |
| 3,915,902 | 10/1975 | Ancel | 252/526 |
| 3,950,185 | 4/1976 | Toyama | 134/38 |
| 4,197,212 | 4/1980 | Minton | 252/164 |

OTHER PUBLICATIONS

Berkeley, B. et al.: "Non-Flammable Paint Strippers", *Soap & Chemical Specialties*, Sep. 1955, pp. 166–169 & 213.

*Primary Examiner*—Dennis L. Albrecht
*Attorney, Agent, or Firm*—Melvin K. Silverman; Joseph A. Giampapa; Alice L. Chen

[57] ABSTRACT

There is disclosed a nail lacquer and enamel remover, composed primarily of methylene chloride combined with various other ingredients such as amyl acetate, butyl acetate, ethyl acetate or acetone and kaydol, aerosol, methyl glucose ether or water. The improvement of the invention as compared with other nail polish removers is that the instant compositions are non-flammable. Such characteristics is not overly important to the product's end user, but represents a significant advance to commercial entities engaged in the specialty cosmetics business, in that manufacture, transport and storage of the product are made safer and less expensive.

3 Claims, No Drawings

NAIL LACQUER AND ENAMEL REMOVER

BACKGROUND OF THE INVENTION

One of the major problems experienced by manufacturers and distributors of nail polish removers is that these substances include in their chemical composition ingredients which are flammable. Due to these flammable ingredients, nail polish removers are treated in commerce as "hazardous" goods; thus at each step in the commercialization process, from product manufacture to retail sale, there is involved additional safety precautions and extra expenses as compared to a nail polish remover of the non-flammable variety.

Prior art attempts at a non-flammable nail polish remover, of which the Applicant is aware include: Japanese Pat. No. 7946846 (1979) to Mitsuwa; Japanese Pat. No. 78145930 (1978) to Mitsuwa; and Soviet Union Pat. No. 642346 (1977) to Uritskaya et. al. However, it is believed that the formula of the instant invention is so sufficiently distinct from prior art compositions that patent protection is warranted.

The present invention is believed to be properly classified in U.S. Class 132, Subclass 75.

SUMMARY OF THE INVENTION

This invention relates generally to nail lacquer and enamel removers, and more specifically to nail lacquer and enamel removers which are non-flammable.

The invention includes a preparation having the following constituents taken in the following proportions:

| Methylene Chloride | 80-90% |
|---|---|
| Amyl Acetate | 9-19% |
| Kaydol (white mineral oil) | 1%. |

The principal object of the invention is to provide a nail lacquer and enamel remover which, while it is as effective (if not more so) as other nail polish removers with respect to removing lacquer or enamel from a consumer's nail, is of a non-flammable chemical composition.

It is another object of the invention to provide a nail polish remover which, due to its non-flammable character, is safer to manufacture, transport and store.

It is a further object of the invention to provide a nail polish remover which, due to its non-flammable character, can be classified as a "non-hazardous" good, thereby reducing the cost of manufacturing, transporting and storing it—as well as reducing the insurance charges associated therewith.

It is a still further object of the invention to provide a nail polish remover which, because of its re-categorization as a non-hazardous good, will be less cumbersome for material handlers to process, thereby expediting the product's shipment within the stream of commerce.

Other objects and advantages of the invention will become more readily apparent from the Detailed Description which follows. It is to be understood, however, that the invention is not limited to the embodiment described below, as it may be embodied in other forms within the scope of the appended claims.

DETAILED DESCRIPTION OF THE PREFERRED EMBODIMENT

I have developed a preparation for the removal of nail lacquer and enamel. This preparation may, in a first embodiment, include the following constituents taken in the following proportions:

| Methylene Chloride | 80-90% |
|---|---|
| Amyl Acetate | 9-19% |
| Kaydol (white mineral oil) | 1%, | which represents the best mode known to the inventor.

The invention may, in a second embodiment, include the following constituents taken in the following proportions:

| Methylene Chloride | 88-93% |
|---|---|
| Kaydol (white mineral oil) | 1% |
| Aerosol (OT 75%) | 1% |
| Butyl Acetate | 5-10% |
| Fragrance - as desired. | |

The invention may, in a third embodiment, include the following constituents taken in the following proportions:

| Methylene Chloride | 89-94% |
|---|---|
| Ethyl Acetate | 5-10% |
| Methyl Glucose Ether | 1% |
| Fragrances - as desired. | |

The invention may, in a fourth embodiment, include the following constituents taken in the following proportions:

| Methylene Chloride | 80-89% |
|---|---|
| Acetone | 5-10% |
| Methyl Glucose Ether | 1-2% |
| Water | 5-10% |
| Fragrance - as desired. | |

The chemical constituents mentioned hereinbefore are commercially available products.

USP white mineral oil is sold under the tradename of Kaydol, manufactured by Sonneborn, a division of Witco Corp.

Aerosol OT 75% is the tradename for sodium dioctyl sulfosuccinate or docusate sodium, as a 75% solution in a water-alcohol solvent. Aerosol is manufactured by Cyanamid.

While the preferred embodiment of the invention has been described, it will be understood that the invention may be otherwise embodied, and that within such other embodiments, certain changes in detail and/or the form and arrangement of the parts may be made without departing from the underlying ideas or principles of this invention within the scope of the appended claims.

Having thus described my invention, what I claim as new, useful and non-obvious and, accordingly secure by Letters Patent of the United States is:

1. A non-flammable nail polish remover for removing nail polish from human nails consisting of

| a, | methylene chloride | 88-93% by weight; |
|---|---|---|
| b, | white mineral oil | 1% by weight; |
| c, | sodium dioctyl sulfosuccinate | 0.75% by weight; and |

| | | |
|---|---|---|
| -continued | | |
| d. butyl acetate | 5–10% by weight. | |

2. A method for removing nail polish from human nails comprising the step of contacting said nails with a non-flammable nail polish remover comprising

| | | |
|---|---|---|
| a. | methylene chloride | 80–90% by weight; |
| b. | amyl acetate | 9–19% by weight; and |

| | | |
|---|---|---|
| -continued | | |
| c. | white mineral oil | 1% by weight. |

3. A method for removing nail polish from human nails comprising the step of contacting said nails with a non-flammable nail polish remover comprising

| | | |
|---|---|---|
| a. | methylene chloride | 88–93% by weight; |
| b. | white mineral oil | 1% by weight; |
| c. | sodium dioctyl sulfosuccinate | 0.75% by weight; and |
| d. | butyl acetate | 5–10% by weight. |

\* \* \* \* \*